United States Patent
Aiyer

(10) Patent No.: US 7,084,979 B1
(45) Date of Patent: Aug. 1, 2006

(54) NON-CONTACT OPTICAL PROFILOMETER WITH ORTHOGONAL BEAMS

(75) Inventor: Arun Ananth Aiyer, Fremont, CA (US)

(73) Assignee: Verity Instruments, Inc., Carrollton, TX (US)

( * ) Notice: Subject to any disclaimer, the term of this patent is extended or adjusted under 35 U.S.C. 154(b) by 355 days.

(21) Appl. No.: 10/301,103

(22) Filed: Nov. 21, 2002

Related U.S. Application Data

(60) Provisional application No. 60/332,646, filed on Nov. 21, 2001.

(51) Int. Cl.
*G01J 4/00* (2006.01)
*G01B 11/24* (2006.01)

(52) U.S. Cl. ...................... 356/369; 356/601

(58) Field of Classification Search ............. None
See application file for complete search history.

(56) References Cited

U.S. PATENT DOCUMENTS

| | | | |
|---|---|---|---|
| 5,017,012 A | 5/1991 | Merritt | |
| 5,777,740 A * | 7/1998 | Lacey et al. ................ | 356/495 |
| 5,955,661 A | 9/1999 | Samsavar | |
| 6,392,749 B1 | 5/2002 | Meeks | |
| 6,464,563 B1 | 10/2002 | Lensing | |
| 6,757,056 B1 * | 6/2004 | Meeks et al. ................ | 356/73 |
| 6,897,957 B1 * | 5/2005 | Meeks ........................ | 356/430 |

* cited by examiner

*Primary Examiner*—Hwa (Andrew) Lee
*Assistant Examiner*—Gordon J. Stock, Jr.
(74) *Attorney, Agent, or Firm*—Rudolph J. Buchel, Jr.

(57) ABSTRACT

An optical profilometer apparatus 10 having a stage with a support surface 42 on which a wafer substrate may rest. The wafer stage is capable of moving the wafer in (x, y) or (r, θ) mode to achieve complete wafer scan. Polarized light from a monochromatic source 12 is directed towards the wafer surface 22. Surface profiling is achieved by sensing beam shift on a segmented sensor caused by level/height change at the wafer surface. In preferred embodiment of the profilometer, a single light beam is engineered to propagate in two orthogonal planes of incidence so that it becomes sensitive to height/level change on the wafer while being insensitive to local slope or wafer tilt. In another embodiment, slope of surface feature is measured. By integrating slope over the measurement spot, local feature height is obtained. This is particularly useful when the beam shift due to feature height change is below detection sensitivity. Since the beam propagates in two orthogonal planes of incidence, the slope measurement sensitivity and hence height sensitivity is doubled. The entire wafer surface can be profiled using (x, y) or (r, θ) scan of the wafer surface.

41 Claims, 4 Drawing Sheets

NON-CONTACT OPTICAL PROFILOMETER WITH ORTHOGONAL BEAMS

CROSS-REFERENCE TO RELATED APPLICATIONS

This application claims the benefit of PPA Ser. No. 60/332,646, filed 2001 Nov. 21 by the present inventor.

FIELD OF THE INVENTION

This invention relates to profiler and methods for topographic measurement, and more particularly to dishing and erosion measurements.

PRIOR ART AND BACKGROUND

The manufacture of semiconductor chips typically involves the repeated imaging of multiple patterned layers on a wafer. Active devices such as transistors, capacitors etc. are formed in the silicon. Once the devices are formed, they are connected via interconnects. Interconnects consist of contact holes and contact lines. As the speed of the CMOS device increases the RC time delay in the interconnects will have to be reduced. To address the latter, chips that use 0.13 μ and smaller design rules, will be using Cu and low k-ILD (Inter-layer Dielectric) in the interconnect. When Cu is used as the wiring metal, removal of excess Cu from places other than vias and trenches is achieved through CMP process. Cu CMP is critical to the successful implementation of dual damascene interconnect process.

In damascene process, Cu is deposited on interlayer dielectric (ILD), for instance tantalum, that has been patterned for vias and/or for lines. After Cu deposition is completed, the wafer surface is planarized via CMP process. The CMP process is expected to remove Cu from the surface while leaving those in vias and lines in tact as shown in FIG. 1. However, in reality, removal rate (RR) of Cu 1 and ILD 3 or the barrier layer 2 are not the same and dishing of Cu line as shown in FIG. 2 is commonly noticed. Difference in RR of layers 2 and 3 will lead to erosion of ILD 3 layer as shown in FIG. 3a. Dishing leads to thinning of metal lines as shown in FIG. 3b and formation of uneven ILD surface for the next level metal as shown in FIG. 4. The latter could affect focus during photolithography at the next metal level. It is also likely that the dimples in the ILD could leave metal puddles after Cu CMP that could lead to shorts between lines. Thinning of Cu line could lead to thermal loading as well as to higher RC time constant. Consequently chip yield will be affected. It is important to be able to measure metal dishing and dielectric erosion so that appropriate measures can be taken to control and minimize these process excursions.

Prior art that are used to measure/monitor dishing and erosion includes Contact Profilometry, Differential Interferometry, and Spectral Reflectometry. Contact profilometer can damage the surface it is contacting and is slow in providing profile data. Differential interferometry using Nomarski Microscope (NM) is a non-contact approach. NM microscope produces fringes that are contours of constant slope in one direction. There are two difficulties with using an interferometer that produces slope fringes. First, slope fringes are difficult to interpret and second, slope must be measured in two directions to fully reconstruct a surface profile. While profiling a semiconductor wafer surface, NM is prone to errors resulting from fringe fading if one spot is incident on a low reflectivity material and the other on a high reflectivity material. A Nomarski surface profiler is described in U.S. Pat. No. 5,017,012, which is incorporated by reference herein in its entirety. Interferometry based on Michelson's or Linnick microscope generally requires complex fringe analysis and is subject to extreme sensitivity to environmental effects, especially vibration and air turbulence. A combination of contact profilometry and optical profilometry in one system is described in U.S. Pat. No. 5,955,661, which is incorporated by reference herein in its entirety. Use of spectral reflectometer in measuring dishing is described in U.S. Pat. No. 6,464,563, which is incorporated by reference herein in its entirety. In this method, grating structure on the wafer surface is illuminated with polychromatic or white light to generate spectral reflectance profile. Dishing in the process layer is determined using a look-up library composed of several reflectance profiles. The disadvantage of this approach is that it mandates a priori knowledge of layers under the grating in order to compute the library profiles. That requirement effectively excludes doing dishing measurement directly on the device structure in the wafer. Reflectometry technique is not useful in measuring dishing of non-grating structure such as wide metal lines. In another optical approach described in U.S. Pat. No. 6,392,749, which is incorporated by reference herein in its entirety, surface profiling is achieved by measuring either the slope or height of surface features with position sensitive segmented detectors. From the slope information, surface topography can be computed. The technique described therein is capable of measuring either height change or slope change. It uses two laser sources and two quad detectors placed in orthogonal planes to measure surface profile. This approach could suffer from errors resulting from source to source and detector to detector variations. The difference signal from the two detectors needs to be processed further to get the height or slope information. In a patterned wafer with grating like structures, reflectivity in one plane (classical) will be significantly different from that on the other plane (conical). This could give rise to detector saturation and light-level control issues. Another embodiment described in the same patent, uses a single laser source and two detectors. Here two different points on the wafer surface are imaged simultaneously. Once the whole wafer surface is scanned, the two images are digitally shifted and subtracted to obtain height information. This approach again is subjected to detector to detector variability error and any error that is associated with the significant amount of post processing that follows data acquisition.

SUMMARY OF INVENTION

Present invention describes an optical method that is non-interferometric, provides high wafer throughput, and can provide information on feature height or feature slope with respect to a reference plane. This invention uses only one laser source and one detector. This significantly simplifies data acquisition and data processing. In accordance with one exemplary embodiment of the invention, a single segmented quad detector senses beam from a laser source after it has propagated through two orthogonal planes of incidence and after it is reflected off of the surface twice. The detection algorithm used in height measurement is such that it is immune to local and global tilt. Thus the output signal of the profilometer in the current invention is direct measure of feature height and need not have to be post processed to extract the same. A variation of this exemplary embodiment allows for slope measurement. By integrating slope over the measurement spot, local feature height information can be obtained. This is particularly useful when the beam shift due to feature height change is below detection sensitivity. Since the beam propagates in two orthogonal planes of incidence, the slope measurement sensitivity and hence height sensitivity is doubled. The entire wafer surface can be profiled using (x, y) or (r, θ) scan of the wafer surface.

DETAILED DESCRIPTION OF PREFERRED EMBODIMENT USED TO PROFILE TOPOGRAPHY OF WAFER SURFACE

Figure 1:
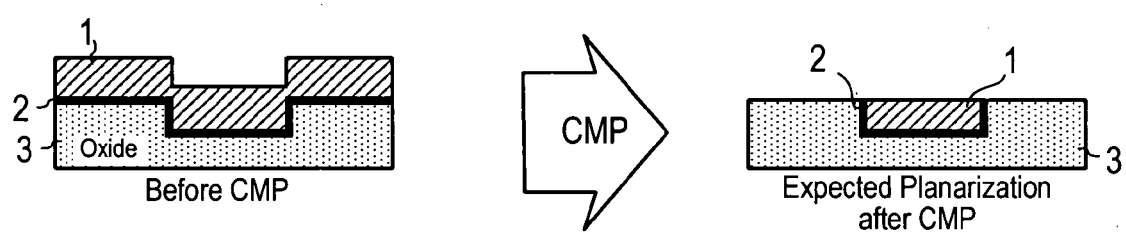
FIG. 1 shows wafer surface before and after Cu CMP
Figure 2:
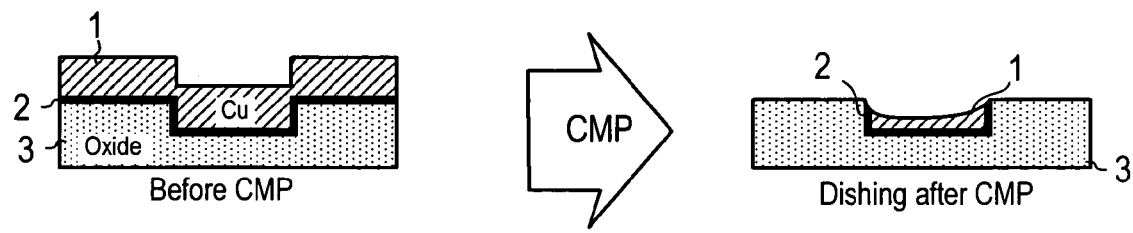
FIG. 2 is shows dishing resulting from CMP process
Figure 3A:
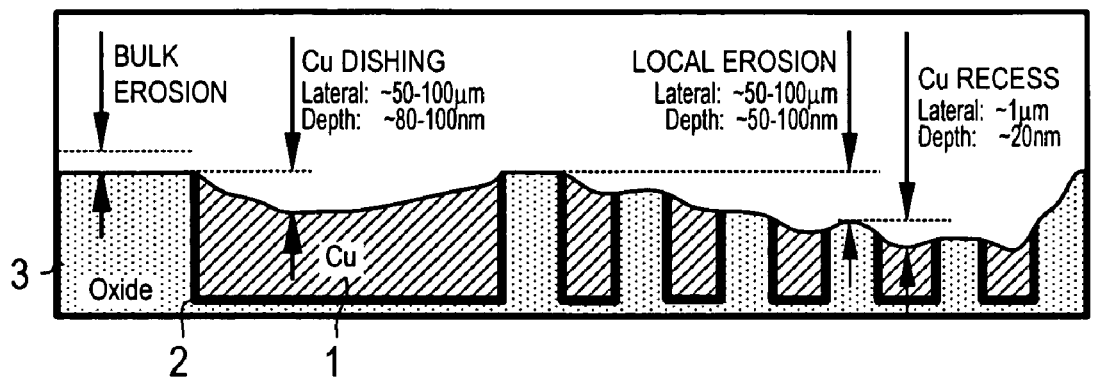
FIG. 3 is a representation of dishing, erosion, metal thinning, local metal recess etc.
Figure 3B:
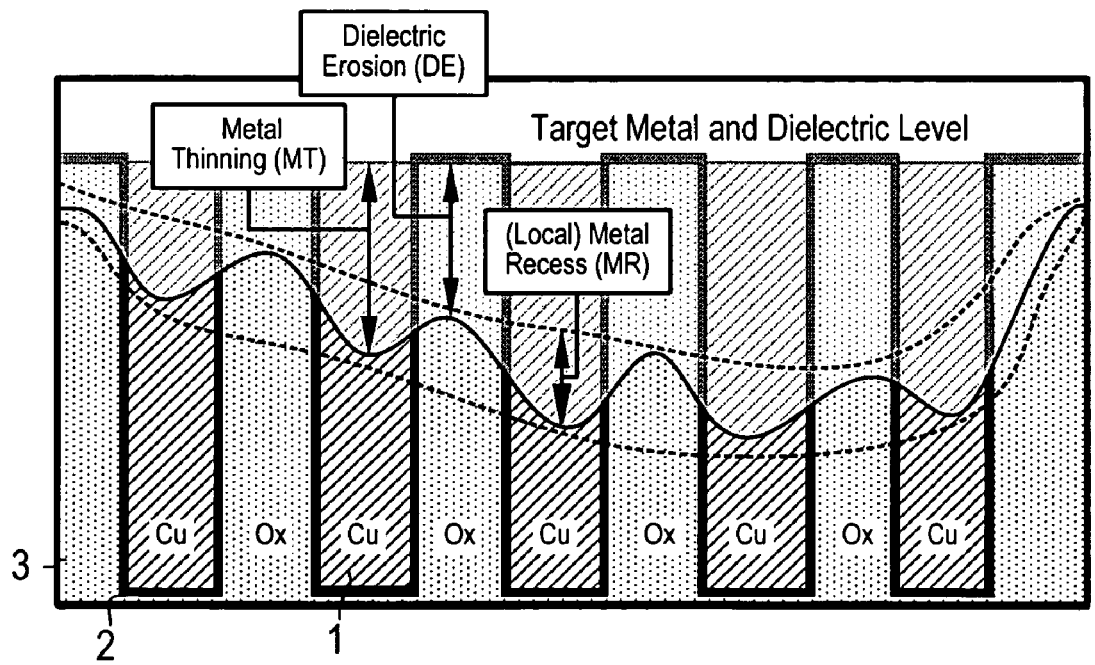
Figure 4:
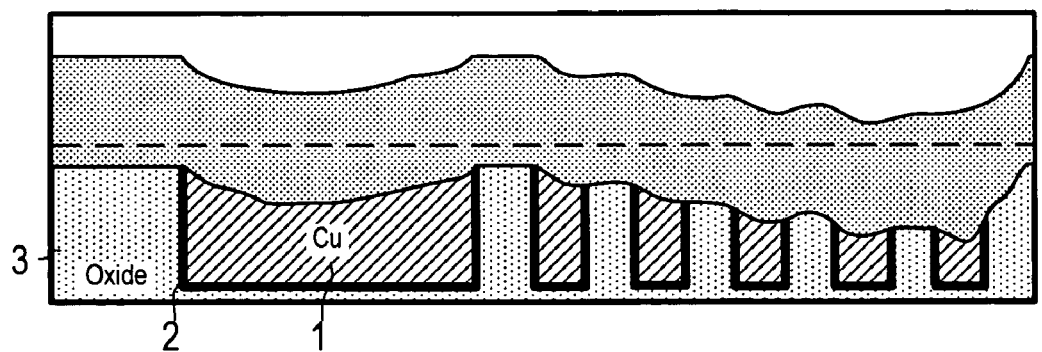
FIG. 4 shows uneven ILD surface resulting from previous level dishing and erosion
Figure 5:
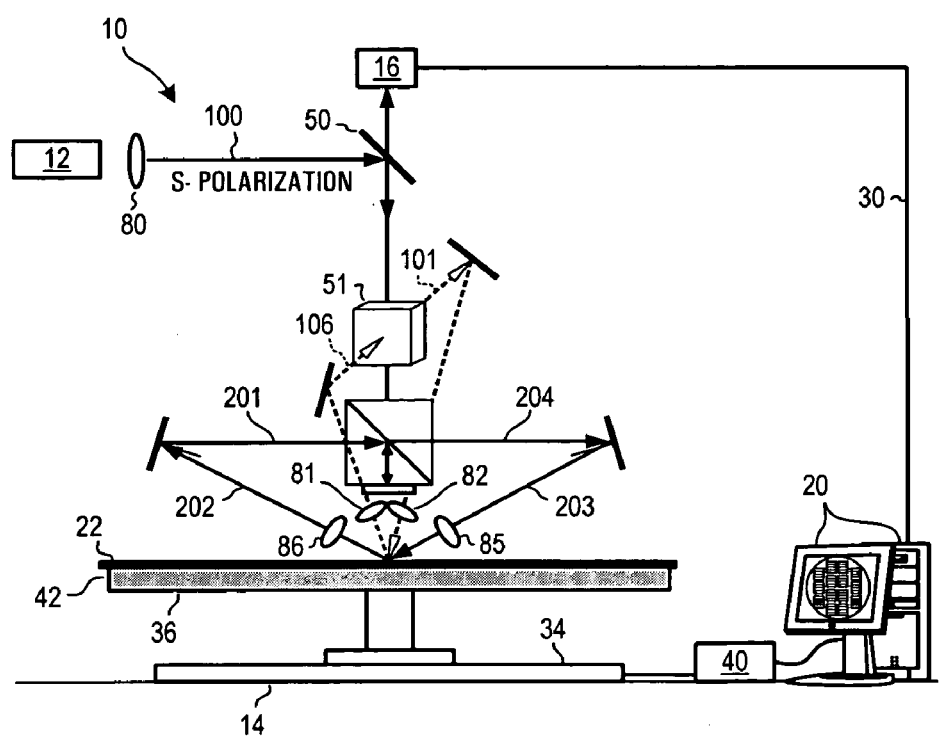
FIG. 5 is a simplified version of present invention in accordance with one exemplary embodiment.

FIG. 5 shows an optical profilometer 10 having a light source 12, a movable (r, θ) or (x, y) wafer support stage 14, a detector 16, and a computer 20. The light source 12 provides a collimated, polarized beam 100 of substantially monochromatic light that is focussed onto a wafer 22, resting on the stage 14, at an oblique angle. The incident beam in the orthogonal plane is focussed using lenses 81 and the reflected light is re-collimated using lenses 82 or vice versa. The incident beam in the plane of the paper is focussed using lenses 85 and the reflected light is re-collimated using lenses 86 or vice versa. The segmented detector 16 is positioned so that it may sense and record the light source specularly reflected from the wafer. The focussed laser spot in conjunction with the moving stage scans the entire wafer surface. In case of rotating stage, the focussed light spot can be moved across the rotating wafer to scan its surface. The detector in communication with a processor can then generate topography of the wafer surface based on beam shift across segments of detector 16.

The light source includes a laser diode (LD) 12 and a set of lenses 80 to produce a collimated beam.

The stage 14 includes a base 34 and a motorized movable wafer support 36 connected to and controlled by the computer 20 via a motor controller 40. The wafer support may be moved in x and y directions or it may be rotated and laterally translated relative to the base for proper positioning and scanning. Alternatively, the wafer support may be rotated and the focussed laser spot laterally translated for proper positioning and scanning. The wafer support 36 has a flat upper surface 42 upon which the wafer rests. The upper surface may include a number of small holes connected to a vacuum pump (not shown) to selectably secure a wafer to the stage for measurement. In each plane of incidence, the incident beam is focussed and re-collimated using lenses 81, 82, 85 and 86.

An ADC card converts signal from the detector 16 into bit map of data, with each pixel (illumination spot) being assigned a difference intensity value corresponding to the level/height change in a small region of the wafer. The bit map data is transmitted to the computer 20 via line 30, so that the computer may make calculations based on the data and store or display the surface topography. The stage and the light source may be contained within a clean enclosure (not shown), with the computer positioned outside the enclosure to minimize contamination of the wafer.

Figure 6:
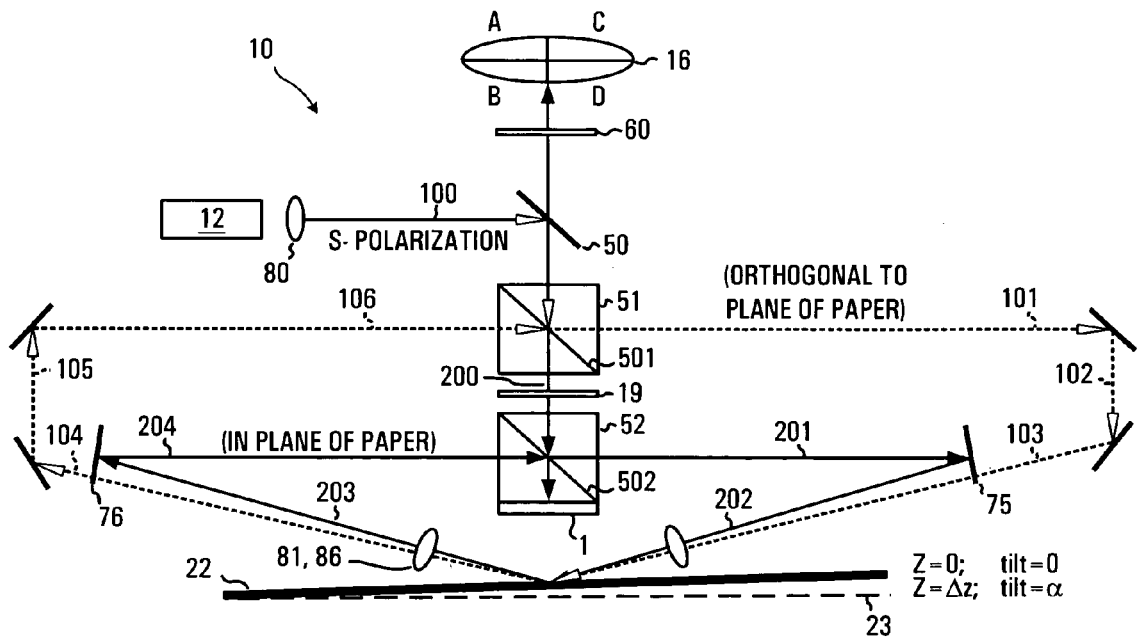
FIG. 6 is a detailed sectional view of the present invention in accordance with another exemplary embodiment.

Principle of operation of the current invention that profiles the wafer surface can be explained using the embodiment 10 in FIG. 5 and its sectional schematic in FIG. 6. Beam paths 101, 102, 103, 104, 105, 106 shown by broken lines are in a plane that is perpendicular to the plane of the paper. Beam paths 201, 202, 203, 204 shown by solid lines are in the plane of the paper. For ease of explanation, both planes of incidence are shown to lie in the plane of the paper. As depicted in the figure, s-polarized collimated beam 100 from a laser 12 (alternatively, collimated beam 100 from laser 12 may be p-polarized (not shown)) is directed toward polarizing beam splitter (PBS) 51 via polarizing beam splitter (PBS) 50. Upon entering PBS 51, it is reflected at interface 501 and traverses the path defined by 101 through 106. The direction of propagation in this plane is along the clockwise CW direction as viewed from the right hand side (using a p-polarized beam would result in the direction propagation for the beams to be reversed in both planes from that shown in the figure).

When the surface moves down, the beam at the detector plane shifts toward the B/D quadrants. Since the profilometer-sensing algorithm is based on difference signal (A+B)−(C+D), it would be insensitive to height or wafer level change.

If the level change is accompanied by a tilt as shown in FIG. 6, it will tilt the plane of incidence and shift the beam at the detector plane toward C/D quadrants. The difference signal based on the above algorithm would represent the wafer tilt. That is the difference signal that "could be" generated by the deflection of orthogonal beams 101–106 due to in-plane tilt and level (height) change is $$S_\perp = (A+B)-(C+D) = -\text{Slope}$$

This means that the detection algorithm used here will contribute only to in-plane tilt of the wafer when the incident beam lies in the orthogonal plane.

Beam 106 upon re-entering PBS 51 is reflected by interface 501 towards PBS 52 as beam 200. Because of λ/2 plate 19, beam 200 is now is again s-polarized with respect to the plane of incidence of PBS 52 and hence will be reflected by interface 502. This reflected beam traverses clockwise the beam paths shown by 201 through 204 in the plane of the paper in the clockwise direction. When the wafer surface moves down, this CW propagating beam would shift the beam toward C/D quadrants at the detector plane. Therefore the difference signal, (A+B)−(C+D), would represent level change Δz. That is $$(A+B)-(C+D) = -\Delta z$$

If the level change is accompanied by a tilt 23, as shown in FIG. 6, it will induce a beam shift toward A/B quadrants at the detector plane. Consequently, the difference signal will also carry information on surface tilt/slope. That is $$(A+B)-(C+D) = \text{Slope}$$

Therefore the difference signal that "could be" generated by the deflection of in-plane beam 201–204 alone due to in-plane tilt and level (height) change is $$S_\parallel = (A+B)-(C+D) = (-\Delta z + \text{Slope})$$

Therefore, the effective detector signal, S, due to beam propagation in both planes would then be $S_\perp + S_\parallel$. That is the difference signal from the quadrant detector 16 is $$|S|=(A+B)-(C+D)=|S_\perp+S_\parallel|=-\text{Slope}\cdot\Delta z+\text{Slope}\cdot\Delta z$$

It should be noted that the s-polarized light 204 reflected off of interface 502 turns into p-polarized light upon reflection at λ/4 plate—HR mirror 1 positioned below PBS 52 and is transmitted by the interface 502. Again, because of λ/2 plate 19, the beam leaving PBS 52 passes through both PBS 51 and PBS 50 to reach the detector 16. Hence transmission losses are minimized.

It is also important to note that in this embodiment, every ray of light that enters PBS 51 is propagated through both (orthogonal) planes of incidence. Consequently, the effective reflectivity of wafer surface with Manhattan geometry is homogenized and the resulting effective surface reflectance is isotropic. Similar result can be achieved by launching p-polarized light into PBS 51 with no λ/2 plate 19 between PBS 51 and PBS 52. In both situations, the beams 103 and 202, incident on the wafer surface are s-polarized. By symmetrically positioning λ/2 plates (not shown) in each incidence plane, p-polarized light can be used to profile the wafer surface.

Figure 7:
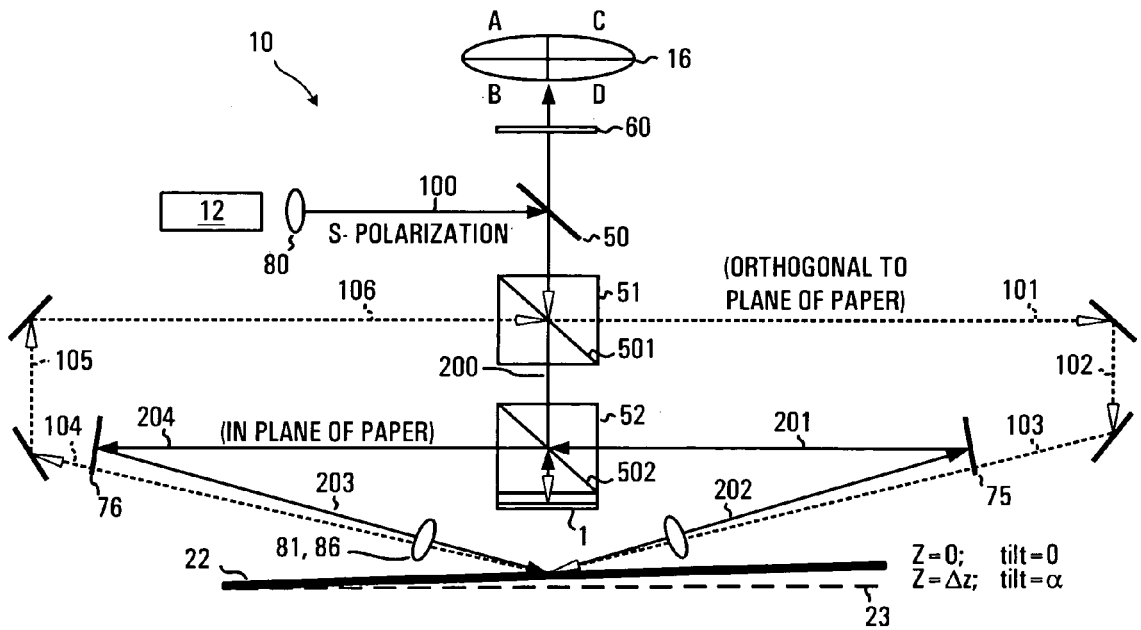
FIG. 7 is a detailed sectional view of the present invention in accordance with still another exemplary embodiment for measuring slope.

A variation to the above embodiment with no half-wave plate 19 positioned between 51 and 52 is shown in FIG. 7.

Here, the difference signal that "could be" generated by the deflection of orthogonal beams 101–106 due to in-plane tilt and level (height) change is $$S_\perp=(A+B)-(C+D)=-\text{Slope}.$$

The difference signal that "could be" generated by the deflection of in-plane beam 201–204 alone due to in-plane tilt and level (height) change is $$S_\parallel=(A+B)-(C+D)=(-\Delta z-\text{Slope})$$

The effective difference signal, S, due to beam propagation in both planes would then be $S_\perp + S_\parallel$. That is the difference signal |S| from the quadrant detector 16 is $$|S|=(A+B)-(C+D)=|S_\perp+S_\parallel|=-\text{Slope}\cdot\Delta z-\text{Slope}=-(2\times\text{Slope}+\Delta z)$$

If beam deflection due to Δz is below detector sensitivity then the detector signal is ∝2×Slope. By integrating this signal, surface profile can be determined. Since the beam propagates in two orthogonal planes of incidence, the slope measurement sensitivity and hence height measurement sensitivity is doubled.

For this embodiment to work effectively, the post reflection beam path-length in the orthogonal plane, between wafer surface 22 and interface 502 needs to be same as the post reflection path-length in the paper plane, between the wafer surface 22 and the detector 16.

A holographic beam homogenizer 60 is positioned in front of segmented detector 16 in order to homogenize any intensity variation that might exist across the cross-section of the reflected beam. This is done to avoid confusion between true beam shift due to topography change and apparent beam shift due to reflection from dissimilar materials.

The latter occurs when part of the beam is incident on highly reflective metal surface and the other part is incident on low reflectance dielectric surface. Homogenizer 60 also helps to avoid error that could be caused by beam shearing in thick dielectric films.

Accordingly, the reader will see that the optical design implemented in this invention provides for an optical profilometer. Furthermore, the invention has the additional advantage that: profiling of the entire wafer surface may be accomplished by means of (r, θ) or (x, v) scan; reflectance variance due to wafer pattern orientation is mitigated by propagating beams in two orthogonal planes of incidence; surface level/height changes are detected directly; wafer pitch and yaw do not affect the measurement (in one embodiment); local tilt does not affect the measurement; dishing and erosion on patterned wafers can be measured with relative ease after CMP; topography can be profiled for any substrate; and allows for continuous auto focus action of wafer surface.

Although the description above contains many specificities, these should not be construed as limiting the scope of the invention but merely as providing illustrations of some of the currently preferred embodiments of this invention.

I claim:

1. An apparatus to measure height of a feature on a surface of a substrate, comprising:
   a stage to support a substrate;
   a polarized light source to generate a polarized light beam;
   first optical components aligned to receive the polarized light beam and to propagate the polarized light beam in a first plane and incident on a first position on the substrate at a first incidence angle and to reflect the polarized light beam off the first position on the substrate at a first reflection angle;
   a polarization state retarder aligned to receive the polarized light beam from the first optical components;
   second optical components aligned to receive the polarized light beam from the polarization state retarder and propagate the polarized light beam in a second plane and incident on the first position on the substrate at the first incidence angle and to reflect the polarized light beam off the first position on the substrate at a second reflection angle, said second plane being substantially orthogonal to the first plane;
   a position sensitive detector aligned to detect the polarized light beam from the second optical components incident on at least one of a plurality of light sensitive locations, said position sensitive detector comprising:
      a plurality of detector elements to convert the polarized light beam into a respective plurality of intensity signals, wherein the plurality of detector elements are arranged with at least a first detector element positioned on a first side of a first separation line and with at least a second detector element positioned on a second side of the first separation line, said first separation line oriented substantially congruent to one of the first plane and the second plane; and
   a processor in communication with the position sensitive detector to receive a plurality of intensity signals from the respective plurality of detector elements and to determine a height of the first position based on a difference signal said difference signal between at least a first intensity signal from the first detector element and a second intensity signal from the second detector element, wherein the difference signal results from a position of the polarized light beam incident on the position sensitive detector, and induced by the first reflection angle in the first plane and the second reflection angle in the second plane.

2. The apparatus of claim 1, wherein said polarized light beam, generated by source by the polarized light source, is one of s- and p-polarization.

3. The apparatus of claim 1 further comprises:
a plurality of lenses aligned in the first plane and aligned in the second plane to focus an incident light beam to the first position and to re-collimate a reflected light to a parallel light beam.

4. The apparatus of claim 1 further comprises;
a rotation and translation mechanism, said rotation and translation mechanism in communication with the processor to receive instructions and connected to the stage to move the stage and substrate in order to propagate the polarized light beam to a second position on the substrate.

5. The apparatus of claim 4, wherein the processor calculates a slope between the first position on the substrate and an adjacent position on the substrate to determine the height of the first position and a second height of the adjacent position, wherein said slope determined by a height difference between the first position and the adjacent position on the substrate and a distance between the first position and the adjacent position on the substrate.

6. The apparatus of claim 4 further comprises:
a holographic diffuser aligned to receive the polarized light beam from the second optical components to homogenize an intensity profile of the polarized light beam incident to the position sensitive detector.

7. The apparatus of claim 6, wherein the first optical components further comprises:
a polarizing beam splitter for reflecting a first polarization state and transmitting a second polarization state.

8. The apparatus of claim 7, wherein the first optical components further comprises:
a second polarizing beam splitter for reflecting the second polarization state and transmitting the first polarization state.

9. The apparatus of claim 8, wherein the polarized light source generates an s-polarized light beam with respect to the first plane and the polarization state retarder retards the polarized light beam to an s-polarized light beam with respect to the second plane.

10. The apparatus of claim 8, wherein the polarized light source generates a p-polarized light beam with respect to the first plane and the polarization state retarder retards the polarized light beam to a p-polarized light beam with respect to the second plane.

11. The apparatus of claim 4, wherein the processor determines a feature profile for the substrate by finding a plurality of difference signals for adjacent positions on the substrate.

12. The apparatus of claim 4, wherein the position sensitive detector further comprises:
at least a third detector element positioned on a second side of a second separation line; and
at least a fourth detector element positioned on a second side of the second separation line, said second separation line oriented substantially congruent to the second plane, wherein the
first and third detector elements are positioned on the first side of the first separation line and
the second and fourth detector elements are positioned on the second side of the first separation line, and
the first and second detector elements are positioned on the first side of the second separation line and
the third and fourth detector elements are positioned on the second side of the second separation line.

13. The apparatus of claim 12, wherein the difference signal further comprises a first cumulative signal and a second cumulative intensity signal, said first cumulative signal derived from a sum of intensity signals detected by at least the first and third detector elements, and said second cumulative intensity signal derived from a sum of intensity signals detected by at least the second and the fourth detector elements.

14. The apparatus of claim 13 further comprises:
a holographic diffuser aligned to receive the polarized light beam from the second optical components to homogenize an intensity profile incident to the position sensitive detector.

15. The apparatus of claim 14, wherein the first optical components further comprises:
a polarizing beam splitter for reflecting a first polarization state and transmitting a second polarization state.

16. The apparatus of claim 15, wherein the second optical components further comprises:
a second polarizing beam splitter for reflecting the second polarization state and transmitting the first polarization state.

17. The apparatus of claim 16, wherein the polarized light source generates an s-polarized light beam with respect to the first plane and the polarization state retarder retards the polarized light beam to an s-polarized light beam with respect to the second plane.

18. The apparatus of claim 16, wherein the polarized light source generates a p-polarized light beam with respect to the first plane and the polarization state retarder retards the polarized light beam to a p-polarized light beam with respect to the second plane.

19. The apparatus of claim 13, wherein the position sensitive detector comprises a plurality of exactly four detector elements.

20. The apparatus of claim 13, wherein the processor determines an absolute height for the first position based on the difference signal and a predefined calibration algorithm.

21. The apparatus of claim 13, wherein the processor determines a feature profile for the substrate by finding a difference signal for adjacent positions on the substrate.

22. A method for measuring a height of a feature on a surface of a substrate comprising:
receiving a polarized light beam;
propagating the polarized light in a first plane incident on a first position on the surface of the substrate at a first incidence angle;
receiving the polarized light reflected from the first position on the substrate at a first reflection angle;
retarding a polarization state of the polarized light beam received from the first position;
propagating the polarized light beam in a second plane incident on the first position on the surface of the substrate at the first incidence angle, said second plane being substantially orthogonal to the first plane;
receiving the polarized light reflected from the first position on the substrate at a second reflection angle;
detecting the polarized light beam incident on at least one of a plurality of light sensitive locations, comprising:
measuring a first intensity at a first location, said first location being located on a first side of a first separation line; and
measuring a second intensity at a second location, said second location being located on a second side of the first separation line, said first separation line oriented substantially congruent to one of the first plane and the second plane; and
determining a height of the first position from a difference intensity measured at the plurality of light sensitive locations, said difference intensity derived between at least the first intensity at the first location and the second intensity at the second location, wherein the difference intensity results from a position of the polarized light beam incident on at least one of the plurality of light sensitive locations and induced by the first reflection angle of polarized light beam in the first plane and the second reflection angle of polarized light beam in the second plane.

23. The method of claim 22, wherein said substrate comprises one of an opaque material and a non-opaque material.

24. The method of claim 22, wherein the polarized light beam is one of an s- and p-polarization.

25. The method of claim 22 further comprises:
moving the substrate in order to propagate the polarized light on a second position on the substrate;
measuring a first intensity of the polarized light beam on the first side of a first separation line;
measuring a second intensity of the polarized light beam on the second side of the first separation line; and
determining a height of the second position on the substrate based upon difference of the first intensity and the second intensity.

26. The method of claim 22 further comprises:
determining a height of an adjacent position to the first position;
calculating a slope at the first position representing a change in height between the first position and the adjacent position on the substrate.

27. The method of claim 25 further comprises:
homogenizing an intensity profile of the polarized light beam incident to the plurality of light sensitive locations.

28. The method of claim 25, wherein propagating the polarized light in the first plane further comprises:
transmitting a first polarization state and reflecting a second polarization state.

29. The method of claim 28, wherein propagating the polarized light in the second plane further comprises:
transmitting the second polarization state and reflecting the first polarization state.

30. The method of claim 29 further comprises:
generating the polarized light beam with s-polarization with respect to the first plane, wherein retarding the polarization state of the polarized light beam retards the polarization state to s-polarization with respect to the second plane.

31. The method of claim 29 further comprises:
generating the polarized light beam with p-polarization with respect to the first plane, wherein retarding the polarization state of the polarized light beam to p-polarization with respect to the second plane.

32. The method of claim 25 further comprises:
measuring a plurality of difference signals for adjacent positions on the substrate;
calculating a plurality of heights for the adjacent positions on the substrate, and
creating a feature profile for the substrate from the plurality of heights.

33. The method of claim 25, wherein detecting the polarized light beam incident on at least one of a plurality of light sensitive locations further comprises:
measuring a third intensity at a third location, said third location being on a second side of a second separation line; and
measuring a fourth intensity at a fourth location, said fourth location being on a second side of the second separation line, said second separation line oriented substantially congruent to the first plane, wherein the first and third locations are on the first side of the first separation line and the second and fourth locations are on the second side of the first separation line, and the first and second locations are on the first side of the second separation line and the third and fourth locations are being on the second side of the second separation line.

34. The method of claim 33, wherein the difference intensity further comprises an intensity difference between a first cumulative intensity and a second cumulative intensity, said first cumulative intensity derived from intensities measured at the first location and the third location, and said second cumulative intensity derived from intensities measured at the second location and the fourth location.

35. The method of claim 34 further comprises:
homogenizing an intensity profile of the polarized light beam incident to the plurality of light sensitive locations.

36. The method of claim 35, wherein propagating the polarized light in the first plane further comprises:
transmitting a first polarization state and reflecting a second polarization state.

37. The method of claim 36, wherein propagating the polarized light in the second plane further comprises:
transmitting a second polarization state and reflecting a first polarization state.

38. The method of claim 37 further comprises:
generating the polarized light beam with s-polarization with respect to the first plane, wherein retarding the polarization state of the polarized light beam retards the polarization state to s-polarization with respect to the second plane.

39. The method of claim 37 further comprises:
generating the polarized light beam with p-polarization with respect to the first plane, wherein retarding the polarization state of the polarized light beam retards the polarization state to p-polarization with respect to the second plane.

40. The method of claim 34, wherein the plurality of light sensitive locations comprises exactly four locations.

41. The method of claim 34 further comprises:
measuring a plurality of difference signals for adjacent positions on the substrate;
calculating a plurality of heights for the adjacent positions on the substrate, and
creating a feature profile for the substrate from the plurality of heights.

* * * * *